United States Patent [19]

Haak et al.

[11] Patent Number: 5,445,606
[45] Date of Patent: * Aug. 29, 1995

[54] INDICATOR FOR IONTOPHORESIS SYSTEM

[75] Inventors: Ronald P. Haak, San Jose; Felix Theeuwes, Los Altos, both of Calif.; David K. Roe, Portland, Oreg.

[73] Assignee: ALZA Corporation, Palo Alto, Calif.

[ * ] Notice: The portion of the term of this patent subsequent to Sep. 21, 2010 has been disclaimed.

[21] Appl. No.: 69,061

[22] Filed: May 28, 1993

Related U.S. Application Data

[63] Continuation of Ser. No. 806,055, Dec. 11, 1991, Pat. No. 5,246,417.

[51] Int. Cl.$^6$ .............................................. A61N 1/30
[52] U.S. Cl. ...................................... 604/20; 607/152
[58] Field of Search ........................... 604/20; 607/152

[56] References Cited

U.S. PATENT DOCUMENTS

| | | | |
|---|---|---|---|
| H 71 | 6/1986 | Sorenson et al. | 604/20 |
| 3,618,601 | 11/1971 | Richardson | 604/20 |
| 3,991,755 | 11/1976 | Vernon et al. | 604/20 |
| 4,116,238 | 9/1978 | Pettijohn | 128/172.1 |
| 4,141,359 | 2/1979 | Jacobsen et al. | 128/172.1 |
| 4,144,317 | 3/1979 | Higuchi et al. | 424/219 |
| 4,250,878 | 2/1981 | Jacobsen et al. | 128/207.21 |
| 4,383,529 | 5/1983 | Webster | 604/20 |
| 4,406,658 | 9/1983 | Lattin et al. | 604/20 |
| 4,456,012 | 6/1984 | Lattin | 128/420 |
| 4,474,570 | 10/1984 | Ariura et al. | 604/20 |
| 4,708,716 | 11/1987 | Sibalis | 604/20 |
| 4,725,263 | 2/1988 | McNichols et al. | 604/20 |
| 4,808,152 | 2/1989 | Sibalis | 604/20 |
| 4,822,334 | 4/1989 | Tapper | 604/20 |
| 4,842,577 | 6/1989 | Konno et al. | 128/803 |
| 4,931,046 | 6/1990 | Newman | 604/20 |
| 4,942,883 | 7/1990 | Newman | 128/798 |
| 5,042,975 | 8/1991 | Chien et al. | 604/20 |
| 5,047,007 | 9/1991 | McNichols et al. | 604/20 |
| 5,135,479 | 8/1992 | Sibalis et al. | 604/20 |
| 5,246,417 | 9/1993 | Haak et al. | 604/20 |

FOREIGN PATENT DOCUMENTS

| | | |
|---|---|---|
| 410009 | 5/1934 | United Kingdom . |
| 2239803 | 7/1991 | United Kingdom . |
| WO91/08795 | 6/1991 | WIPO ........................... A61N 1/30 |
| 9115259 | 10/1991 | WIPO . |

OTHER PUBLICATIONS

Dorland's Pocket Medical Dicitonary, 23rd Ed., p. 362.

*Primary Examiner*—Corrine Maglione
*Assistant Examiner*—Mark W. Bockelman
*Attorney, Agent, or Firm*—D. Byron Miller; Steven F. Stone; Edward L. Mandell

[57] ABSTRACT

Apparatus (11) for delivery of a medicament, drug or other therapeutic agent transdermally to a body by iontophoresis is provided. The apparatus (11) provides a means (13) for measuring and displaying the cumulative amount of the medicament delivered to the body by monitoring the amount of a metal, initially present at the anode (45), that is transferred to the cathode (41) in a subsidiary electrolyte cell (47) through which the drive current for the apparatus (11) passes. Optionally, the apparatus also provides a plurality of light emitting devices (63-1) that display a measure of the cumulative amount of medicament delivered, by use of visually distinguishable light colors or by use of binary encoding in the light display.

33 Claims, 1 Drawing Sheet

INDICATOR FOR IONTOPHORESIS SYSTEM

This is a continuation of U.S. patent application Ser. No. 07,806,055 filed Dec. 11, 1991 now U.S. Pat. No. 5,246,417.

TECHNICAL FIELD

This invention relates to an improved method for displaying the amount of drug delivered transdermally by iontophoresis.

BACKGROUND ART

Iontophoresis is defined by Dorland's *Illustrated Medical Dictionary* as "the introduction, by means of electric current, of ions of soluble salts into the tissues of the body for therapeutic purposes." Iontophoretic devices have been known since the early 1900's. British patent specification No. 410,009, published in 1934, describes an iontophoretic device that overcame one of the disadvantages of such early devices known to the art at that time, namely the requirement of a special low tension (low voltage) some of current which meant that the patient needed to be immobilized near such source. In that British specification, the device was made by forming a galvanic cell from two electrodes plus the material containing the medicament or drug to be transdermally delivered. The galvanic cell produced the current necessary for iontophoretically delivering the medicament. This ambulatory device thus permitted iontophoretic drug delivery with substantially less interference with the patient's daily activities.

The iontophoresis process has been found to be useful in the transdermal administration of medicaments or drugs including lidocaine hydrochloride, hydrocortisone, fluoride, penicillin, dexamethasone sodium phosphate and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

Presently known iontophoretic devices use at least two electrodes, positioned in intimate contact with some portion of the skin of the body. A first electrode, called the active or donor electrode, delivers the ionic substance, medicament, drug precursor or drug into the body by iontophoresis. The second electrode, called the counter or return electrode, closes an electrical circuit including the body, the first electrode and a source of electrical energy, such as a battery. For example, if the ionic substance to be driven into the body is positively charged, the anode will be the active electrode and the cathode will serve as the counter electrode to complete the circuit. If the ionic substance to be delivered is negatively charged, the cathode will be the active electrode and the anode will be the counter electrode.

Alternatively, both the anode and cathode may be used to deliver drugs of opposite electrical charge into the body. In this situation, both electrodes are considered to be active or donor electrodes. For example, the anode can drive a positively charged ionic substance into the body, and the cathode can drive a negatively charged ionic substance into the body.

It is also known that iontophoretic delivery devices can be used to deliver an uncharged drug or agent into the body. This is accomplished by a process known as electroosmosis. Electroosmosis is the transdermal flux of a liquid solvent (e.g., the liquid solvent containing the uncharged drug or agent) that is induced by the presence of an electrical field imposed across the skin by the donor electrode. As used herein, the terms "iontophoresis" and "iontophoretic" refer to (1) the delivery of of charged drugs or agents by electromigration, (2) the delivery of uncharged drugs or agents by electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

Existing iontophoresis devices generally require a reservoir or source of the ionized or ionizable species, or a precursor of such species, that is to be iontophoretically delivered or introduced into the body. Examples of such reservoirs or sources of ionized or ionizable species include a pouch as described in the previously mentioned Jacobson patent, U.S. Pat. No. 4,250,878, issued to Jacobsen, or a pre-formed gel body as disclosed in U.S. Pat. No. 4,383,529, issued to Webster. Such reservoirs are electrically connected to the anode or the cathode of an iontophoresis device to provide a fixed or renewable source of one or more desired species.

Recently, transdermal delivery of peptides and proteins, including genetically engineered proteins, by iontophoresis has received increasing attention. Generally speaking, peptides and proteins being considered for transdermal or transmucosal delivery have a molecular weight ranging between about 500 to 40,000 Daltons. These high molecular weight substances are too large to passively diffuse through skin at therapeutically effective levels. Because many peptides and proteins carry either a net positive or net negative charge, but are unable to passively diffuse through skin, these substances are considered likely candidates for iontophoretic delivery.

Iontophoresis is now being considered for long term delivery, over periods of longer than 24 hours, of a number of drugs, including peptides and proteins (e.g., insulin). As the length of delivery increases, there is a need to develop small unobtrusive iontophoretic delivery devices which can be easily worn on the skin under clothing. One example of a small iontophoretic delivery device designed to be worn on the skin is disclosed in U.S. Pat. No. 4,474,570, issued to Ariura et al. Devices of this type are powered by small, low voltage batteries. In addition to the need for developing smaller iontophoretic delivery devices, there is a need to reduce the cost of these devices in order to make them more competitive with conventional forms of therapy such as pills and subcutaneous injections.

One method of reducing cost is to use even lower voltage power sources. Unfortunately, as the power source voltage decreases, the drug delivery rate also decreases. Thus, there is a need for a method of improving the performance characteristics, such as the amount of drug delivered per unit of power, of iontophoretic delivery devices to enable the use of inexpensive low-voltage power sources. Further, a particular need exists for monitoring the amount of medicament delivered, especially when the amount delivered can vary or does not follow a predetermined pattern, as in a patient-controlled (on-demand) and feedback-controlled delivery system.

One method of increasing the rate at which drug is delivered from a transdermal iontophoretic drug delivery device is to apply the device on a skin site having optimum drug transport characteristics. For example, in International Patent Publication No. WO 91/08795, R. P. Haak et al discuss optimum skin sites for attaching an iontophoretic drug delivery device to a human patient. In a human patient, the patient's back appears to be the optimum site for electrically assisted drug delivery, although the back does not have the highest density of sweat ducts or skin pores for iontophoretic transport.

During long-term iontophoretic drug delivery, it is difficult to accurately estimate beforehand the amount of drugs that will be delivered by iontophoresis over a selected time interval such as 24 hours. For example, either by design or because of uncontrollable factors, such as battery discharge characteristics, the current used to drive the iontophoresis process may vary over this time interval. Further, environmental conditions, such as humidity, temperature, perspiration and wetness, due to bathing, adjacent to the delivery site may also vary with time. Either of these uncertainties may produce uncertainties in the amount of drug or medicament absorbed by the body over a long time interval.

Some workers have attempted to handle these uncertainties by providing feedback regulation or polarity reversal of the applied voltage so that the current, and thus the rate of delivery of drug/medicament by iontophoresis, is kept approximately uniform over a selected time interval. Polarity is sometimes reversed to avoid skin irritation and to depolarize the skin. Skin polarization is an obstacle to efficient electrotransport drug delivery. Polarity control is disclosed in U.S. Pat. No. 4,116,238, issued to Pettijohn, in U.S. Pat. No. 4,141,359, issued to Jacobsen, et al., in U.S. Pat. No. 4,406,658, issued to Lattin, et al., and in U.S. Pat. No. 4,456,012, issued to Lattin. The complex electronics required here uses devices such as transformers and SCR rectifiers, and it may not be convenient or even possible to provide this in a compact, lightweight package that can be worn by the patient under clothing.

Other workers have provided means for selectively varying the current delivered by the applied voltage near the site. McNichols et al., in U.S. Pat. No. 4,725,263, disclose use of a current control module for iontophoresis that can be mechanically trimmed in order to change the current level used for this process. However, only a small number, such as three, preselected current values may be chosen, and the choice of current level usually cannot be reversed. The mechanical trimming also serves as a simple visual indicator of which current level has been chosen.

Sibalis discloses provision of a third electrode in a parallel current loop in the iontophoresis process, in U.S. Pat. No. 4,708,716. This parallel current loop provides a feedback signal that assertedly indicates when a desired dosage level is achieved in the blood serum. A reverse plating cell is used here, in which the resistance to current flow from anode to cathode increases abrupdy as metal or another electrically conductive material is transferred (with the accompanying electrical charge) from an active electrode to a counter electrode. However, this indicator, which relies on an abrupt increase in resistance to charge flow, appears to provide only two indicator levels.

An electronic control system for limiting total iontophoretic dose is disclosed by Tapper in U.S. Pat. No. 4,822,334. The system includes a voltage controlled osciallator whose oscillation frequency is proportional to the current delivered to a load, such as a patient's body that is receiving the dose. The number of VCO cycles in a given time interval is counted to determine the load current presently applied to and the dose delivered during that time interval.

U.S. Pat. No. 4,942,883, issued to Newman, discloses use of a sensing means in a housing for an iontophoretic device to alternatingly turn on and turn off the current that delivers the drug or medicament. The frequency of alteration of current turn on and turn off may be of the order of 50 kHz, and may be controlled by an on-board microprocessor.

The devices discussed above are often bulky and do not provide a continuous indicator of cumulative dose delivered by iontophoresis. What is needed is a compact, lightweight iontophoretic apparatus that provides a continuous indicator of cumulative dose delivered and, perhaps, of the status of certain other system variables, and that can easily be worn adjacent to the delivery site for the drug, medicament or other therapeutic agent

DESCRIPTION OF THE INVENTION

These needs are met by the invention, which in one embodiment includes first and second electrode assemblies electrically connected to a source of electrical current. At least one of the fast and second electrode assemblies contains a therapeutic agent to be delivered to a patient. The electrode assembly that contains the therapeutic agent is adapted to be placed in therapeutic agent transmitting relation with a body surface of the patient. The other electrode assembly is adapted to be placed in ion transmitting relation with the body surface at a location spaced apart from the electrode assembly containing the therapeutic agent. A display module is electrically connected between the current source and one of the electrode assemblies. The display module displays the cumulative amount of charge transferred through the module. The measurement and display of cumulative transferred charge or current may be performed by transfer of metal ions, such as copper ions, from an anode to a cathode within the display module as the metal ions flow from cathode to anode through a liquid electrolyte.

In another embodiment, a signal representing the cumulative current $\Delta Q$ that has passed through the medicament layer drives a plurality of visible light devices (light emitting diodes, liquid crystals, etc.) to display quantitatively a measure of $\Delta Q$. This visual display may be color coded, using a plurality of devices that display different colored light to indicate the present range that $\Delta Q$ lies in. Alteratively, the plurality of visible light devices may be binary coded to display the present range of $\Delta Q$ as a binary number, or to display both the present range of $\Delta Q$ and the status of other selected system variables affecting system performance or accuracy.

MODELS FOR CARRYING OUT THE INVENTION

Figure 1:
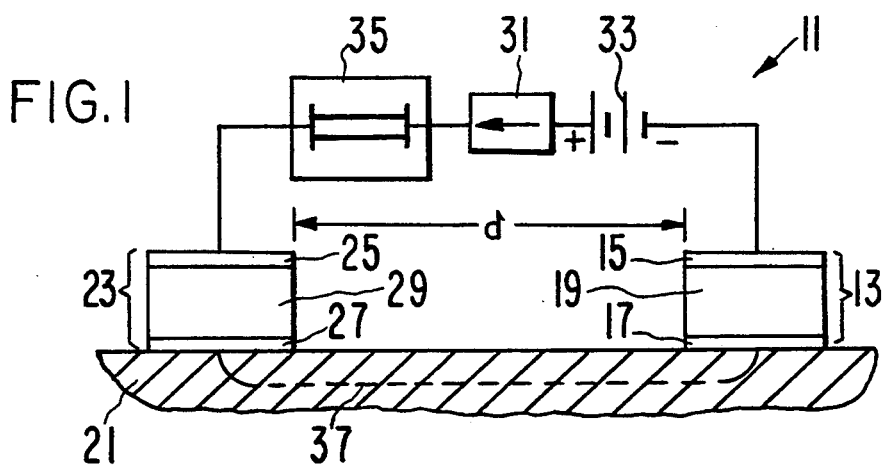
FIGS. 1 and 6 illustrate alternative embodiments of the invention.

FIG. 1 illustrates a first embodiment 11 of the invention, including a current controller 31 (optional), a current source 33, a display module 35 and first and second electrode assemblies 13 and 23. For purposes of illustration, the first or donor electrode assembly 13 includes an electrically conducting layer 15, an ion-conducting adhesive layer 17 (optional) and a medicament layer 19 positioned between and in electrical contact with the electrically conducting layer 15 and either the adhesive layer 17 or the patient's body 21. The medicament layer 19 contains one or more medicaments, drags or other therapeutic agents that is to be delivered transdermally to the body 21 by iontophoresis. The second or counter electrode assembly 23, includes an electrically conducting layer 25, an ion-conducting adhesive layer 27 (optional) and a layer 29 containing an electrolyte salt. Alternatively, the layer 29 may contain another medicament, drug or other therapeutic agent. Electrolyte layer 29 is positioned between and electrically connected to the electrically conducting layer 25 and either the adhesive layer 27 or the patient's body. The second electrode assembly 23 is spaced apart from the first electrode assembly 13 by a suitable distance d that may be 0.5 mm–10 cm, although this distance is not critical. The electrode assemblies 13 and 23 are positioned so that their respective ion-conducting adhesive layers 17 and 27, if present, are directly in contact with the patient's body 21. If the adhesive layer 17 or 27 is deleted, the corresponding medicament layer 19 or electrolyte layer 29, respectively, directly contacts the body, e.g., the skin. In either case, the layers 19 and 29 are each in ion transmitting relation with the surface of the body 21.

Electrically conducting layers 15 and 25 may be formed of a metal, such as a metal foil or metal deposited or painted on as a suitable backing. Examples of suitable metals include zinc, silver, silver/silver chloride, aluminum, platinum, stainless steel, gold and titanium. Alternatively, the electrically conducting layers 15 and 25 may be formed of a hydrophobic polymer matrix containing a conductive filler, such as metal powder, powdered graphite, carbon fibers or other known electrically conductive filler material. The hydrophobic polymer-based electrodes may be made by mixing the conductive filler in the hydrophobic polymer matrix. For example, zinc powder, silver powder, silver/silver chloride powder, powdered carbon, carbon fibers or mixtures thereof can be mixed in a hydrophobic polymer matrix, such as polyisobutylene rubber, with the preferred amount of conductive filler being within the range of 30–90 volume percent and the remainder being the hydrophobic polymer matrix.

The electrically conducting layers 15 and 25 are electrically connected to the current source 33, to the display module 35 and to the optional current controller using well known means, for example, by printed flexible circuits, metal foils, wires or electrically conductive adhesives, or by direct contact. The battery current source 33 may be supplemented by a galvanic couple formed by conducting layers 15 and 25 that are composed of dissimilar electrochemical couples. Typical galvanic couple materials for delivering a cationic agent include a zinc conducting layer 15 and a silver/silver chloride conducting layer 25. A Zn-Ag/AgCl galvanic couple provides an electrical potential of about one volt.

Regardless of the source of electrical current used, the current source 33 in combination with the electrode assemblies 13 and 23 and the patient's body completes the circuit and generates an electrical field across the body surface or skin to which the device 11 is applied. This electrical field runs from the current source 33, through the display module 35, through the electrically conducting layer 25, through the electrolyte layer 29, through the adhesive layer 27, through the body of the patient, through the adhesive layer 17, through the therapeutic agent-containing layer 19, through the electrically conducting layer 15 and back to the current source 33. The electrical field generated by the current source 33 causes the therapeutic agent within the layer 19 to be delivered through the adhesive layer 17 (optional) and into the body by the process of iontophoresis.

Each of the medicament layer 19 and the electrolyte layer 29 preferably comprises a polymer matrix loaded with either a therapeutic agent or with an electrolyte salt. The polymer matrix of layers 19 and 29 may be comprised of a hydrophilic polymer, preferably a mixture of a hydrophilic polymer and a hydrophobic polymer, and most preferably a mixture of about 10–60 dry weight percent of a hydrophilic polymer and about 10–60 dry weight percent of a hydrophobic polymer. The medicament layer 19 and the electrolyte layer 29 include a matrix that typically contains 0.5–60 dry weight percent drug and 0.5–60 dry weight percent electrolyte, respectively.

As used herein, a hydrophilic polymer is a polymer having an equilibrium water content of at least 20 weight percent, preferably at least 30 weight percent, and most preferably at least 40 weight percent, after prolonged exposure to an atmosphere having a relative humidity of over 90 percent. As used herein, a hydrophobic polymer is a polymer having an equilibrium water content of less than 20 weight percent, preferably less than 15 weight percent, and most preferably less than 10 weight percent, after prolonged exposure to an atmosphere having a relative humidity of over 90 percent.

Preferably the hydrophobic polymer is heat fusible and can be heat fused to another polymer surface, such as a polymer-based electrode or membrane. Alternatively, if the electrically conducting layers 15 and 25 in FIG. 1 are composed of a metal, such as a metal plate, a metal foil or a metallized surface on a suitable backing material, the hydrophobic polymer may require a resinous tackifying agent.

Suitable hydrophobic polymers for use in the matrices of the therapeutic agent layer 19 and the electrolyte layer 29 include, without limitation, the following polymers: polyethylene; polypropylene; polyisoprenes; polyalkenes; robbers; copolymers such as Kraton®, polyvinylacetate and ethylene vinyl acetate copolymers; polyamides such as nylons; polyurethanes; polyvinylchloride; acrylic or methacrylic resins such as polymers of esters of acrylic or methacrylic acids with alcohols such as n-butanol, n-pentanol, isopentanol, isopentanol, 2-methyl butanol, 1-methyl butanol, 1-methyl pentanol, 2-methyl pentanol, 3-methyl pentanol, 2-ethyl butanol, isooctanol, n-decanol or n-dodecanol, alone or copolymerized with ethylenically unsaturated monomers such as acrylic acid, methacrylic acid, acrylamide, methacrylamide, N-alkoxymethyl acrylamides, N- alkoxymethyl methacrylamides, N-tert-butylacrylamide and itaconic acid; N-branched alkyl maleamic acid, wherein the alkyl group has 10–24 carbon atoms; glycol diacrylates; and blends thereof. Most of the above-listed hydrophobic polymers are heat fusible. Of the heat fusible, hydrophobic polymers, polyisobutylene rubbers and ethylene vinyl acetate copolymers are preferred.

Where the electrically conducting layers 15 and 25 are metal foils or metallized polymeric films, it may be necessary to add a tackifying resin to the hydrophobic polymer component in order to enhance its adhesiveness. Suitable hydrophobic polymers that can be rendered more adhesive by the addition of tackifying resins include, without limitation, the following: cellulose acetate butyrate; ethylcellulose; polyurethanes; poly(styrene-butadiene) and poly(styrene-isoprene-styrene) block copolymers; ethylene vinyl acetate copolymers, such as those described in U.S. Pat. No. 4,144,317, issued to Higuchi et at; plasticized or unplasticized polyvinylchloride; natural or synthetic rubbers; and $C_2$–$C_4$ polyolefins, such as polyethylene, polyisoprene, polyisobutylene and polybutadiene. Examples of suitable tackifying resins include, without limitation, fully hydrogenated aromatic hydrocarbon resins, hydrogenated esters and low molecular weight grades of polyisobutylene. Particularly suitable are tackifiers sold by Hercules, Inc. of Wilmington, Del. under the trademarks Staybellite Ester ® #5 and #10, Regal-Rez ® bad Piccotac ®.

Suitable hydrophilic polymers for use in the matrices for the layers 19 and 29 in FIG. 1 include the following: polyvinylpyrrolidones; polyvinyl alcohol; polyethylene oxides, such as Polyox ®, manufactured by Union Carbide, and Carbopol manufactured by B.F. Goodrich of Akron, Ohio; blends of polyoxyethylene or polyethylene glycols with polyacrylic acid, such as Polyox ® blended with Carbopol ®; polyacrylamide; Klucel ®; cross-linked dextran, such as Sephadex (from Pharmacia Fine Chemicals, AB, Uppsala, Sweden) or Water Lock ® (from Grain Processing Corp., Muscatine, Iowa), which is a starch-graft-poly(sodium acrylate-co-acrylamide) polymer; cellulose derivatives, such as hydroxyethyl cellulose, hydroxypropymethyl cellulose and low-substituted hydroxypropylcellulose; cross-linked Na-carboxymethylcellulose, such as Ac-Di-Sol (from FMC Corp., Philadelphia, Pa.); hydrogels, such as polyhydroxyethyl methacrylate (from National Patent Development Corp.), natural gums; chitosan; pectin; starch; guar gum; locust bean gum and the like; and blends thereof. Of these, the polyvinylpyrrolidones are preferred.

Blending of the drug or electrolyte with the polymer matrix is done mechanically, either in solution or by milling, extrusion or hot melt mixing, for example.

The layers 19 and 29 may contain, in addition to the drug and electrolyte, other conventional materials, such as dyes, pigments, inert fillers and other excipients.

The electrically conducting layer 15 of the first electrode assembly 13 serves as an electrical contact for, and is electrically connected to, a first current-carrying terminal of a current controller 31 (optional) or of current source 33. A second current-carrying terminal of the current controller 31 is electrically connected to a first terminal (cathode or anode) of a battery or other current source 33. The current controller 31, which may be externally controllable or may be internally configured to work automatically, controls the rate of charge flow between its first and second terminals. This permitted rate of charge flow may range between two predetermined limits, such as 0.1 milliamps and 1 milliamp "mA"), or may be more precisely controlled by a simple feedback circuit, including a differential amplifier with a voltage input signal to one input terminal that is used to control a current output signal in a static or time-varying manner.

The current source 33, possibly regulated by the optional current controller 31, may be a simple battery that provides a substantially constant voltage difference between the first terminal and a second terminal, or the current source 33 may provide a time-varying current that varies slowly and in a pre-programmed manner with time. Alternatively, the current source 33 and current controller 31 may provide a current that varies between predetermined lower and upper limits. The second terminal of the current source 33 is electrically connected to a first terminal of a display module 35 that measures and/or visually displays the cumulative amount of electrical charge transferred from its fast terminal to a second terminal of the display module 35. A second terminal of the display module 35 is connected to the electrically conducting layer 25 of the second electrode assembly 23. A dermal or sub-dermal electrical path 37 in the patient's body 21 completes an electrical circuit that includes the donor electrode assembly 13, the current source 33, the display module 35 and the counter electrode assembly 23, shown in FIG. 1.

Figure 2:
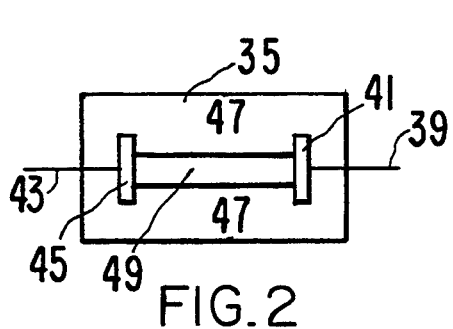
FIG. 2 is a more detailed view of a display module that is part of the embodiment shown in FIG. 1.

FIG. 2 illustrates an embodiment of the display module 35 of FIG. 1 in more detail. The display module 35 receives electrical charge on a first current-carrying line 39 that is electrically connected to a cathodic terminal 41 of the module 35. The display module 35 transfers electrical charge to a second current-carrying line 43 that is electrically connected to an anodic terminal 45. The anodic terminal 45 preferably includes a metal coating of copper, silver, nickel, mercury, chromium, iron, lead, tin or similar material, and the cathodic terminal 41 may be a different, electrically conducting material. Electrical charge is transferred from anodic terminal to cathodic terminal through oxidization and reduction of chemical species. An ionic species is generated by the oxidization reaction at the anodic terminal 45. This ionic species is then conducted through an electrolyte solution 47 positioned between the cathodic terminal 41 and the anodic terminal 45. The conducted ionic species is consumed by the reduction reaction occurring at the cathodic terminal 41. The solution 47 may initially contain dissolved cations, such as $Cu^+$, which are subsequently electroplated onto the cathodic terminal 41 to provide improved initial response of the iontophoretic transport of the medicament. The electrolyte solution 47 may be any conventional electroplating bath solution, including but not limited to sulfuric acid, citric acid, phosphoric acid, pyrophosphoric acid, fluoboric acid, oxalic acid cyanide or ammonium hydride. If a cation is to be dissolved in the electrolyte solution, the electrolyte itself should be chosen based upon the choice of cation. A tube or other flow enhancement means 49 (optional) may be positioned between the anodic terminal 45 and the cathodic terminal 41 to promote and control flow to the cathodic terminal 41 of the metal cations liberated at the anodic terminal 45.

As the liberated cations accumulate at the cathodic terminal 41 and are reduced electrochemically, i.e., electroplated, the cumulative mass of these ions thereat can be quantitatively displayed by visual means. The cumulative mass of these ions is approximately proportional to the time integral of the current i(t), viz.

$$\Delta Q(t) = \int i(t')dt \quad (1)$$

between anodic terminal and cathodic terminal for the time interval $[t_0, t]$ of interest. The incremental charge $\Delta Q$ in Eq. (1) is measured in Coulombs, and the Coulomb-measuring device 35 shown schematically in FIG. 2 should consume less than 100 millivolts in operation. The embodiment 11 shown in FIG. 1 can easily be incorporated into a transdermal iontophoresis device. If visual display means for the cumulative charge $\Delta Q$ is to be provided, the display module 35 should be provided with a transparent backing material, such as clear plastic, for one surface.

Growth of the metal ions deposited on the cathodic terminal 41 is approximately related to the time-integrated current $\Delta Q$ by the relationship $$\Delta m = (M/ZF)\Delta Q, \quad (2)$$

where
$\Delta m$ = cumulative mass of ions deposited at cathodic terminal,
Z = oxiditation state of metal ion to be deposited on cathodic terminal,
F = Faraday constant = 96,487 Coulombs per equivalent,
M = atomic weight of anode metal coating (e.g., 63.5 for Cu).

For example, 10 hours of uniform current of 1 mA will produce a cumulative mass deposit $\Delta m$ of 11.8 micrograms of Cu at the cathodic terminal. For some anode metals of interest, then, $\Delta m$ and $\Delta Q$ are approximately linearly related by the equations $$\Delta m = k \Delta Q, \quad (3)$$

where k is a material constant given by $$k = M/ZF. \quad (4)$$

The k values for the preferred metal coatings for the invention are as follows.
k = 3.29 × 10$^{-4}$ (Cu),
k = 1.18 × 10$^{-4}$ (Ag),
k = 3.04 × 10$^{-4}$ (Ni),
k = 1.03 × 10$^{-3}$ (Hg),
k = 1.79 × 10$^{-4}$ (Cr),
k = 2.09 × 10$^{-4}$ (Fe),
k = 1.07 × 10$^{-3}$ (Pb),
k = 6.15 × 10$^{-4}$ (Sn).

The relationship between cumulative ion mass $\Delta m$ and time-integrated current $\Delta Q$ need not be linear, as suggested in Eq. (2), as long as cumulative ion mass $\Delta m$ is a known, strictly monotonically increasing function of $\Delta Q$. A variable y=f(x) is said to be a monotonically increasing function of the variable x if, for any two values $x_1$ and $x_2$ for which f(x) is defined with $x_1 < x_2$, the inequality $f(x_1) \leq f(x_2)$ holds; y=f(x) is strictly monotonically increasing if $x_1 < x_2$ implies $f(x_1) < f(x_2)$.

Several control features are central to operation of this invention. First, action of the channel for metal deposited on the cathodic terminal, defined by the tube 49 in FIG. 2, must be reproducible. Second, the anodic terminal 45 and cathodic terminal 41 must be reproducibly fabricated. Third, the composition of the liquid electrolyte 47 positioned between and surrounding the anodic terminal 45 and cathodic terminal 41 should be chosen to produce a smooth, uniform deposit of metal ions on the cathodic terminal.

Figure 3:
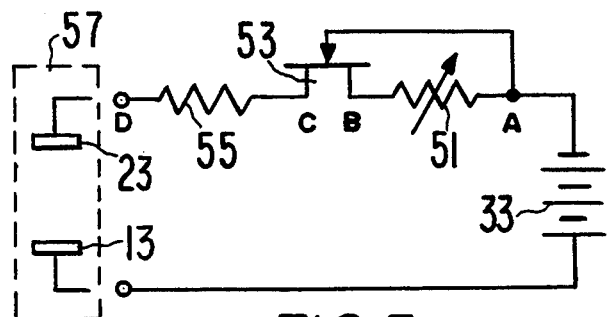
FIG. 3 illustrates one embodiment of a circuit suitable for providing the current used to drive the invention.

FIG. 3 illustrates one suitable circuit that can be used for the current controller 31 shown in FIG. 1. The current source 33 of FIG. 1 may, for example, be three Li batteries connected in series to provide a voltage difference of approximately 9 Volts, with the low voltage electrode of the battery being connected across a resistor 51 to the source of an junction field effect transistor ("JFET") 53. The current source 33 is connected directly to the gate of the JFET 53. The resistor 51 may have a variable resistance, with an impedance swing of 100 kilo-ohms, or may have a fixed resistance value in the range of 10–100 kilo-ohms. The JFET 53 may be the 2N4220 or any equivalent transistor. The drain of the JFET 53 is connected across a current-measuring and current-limiting resistor 55 (optional), preferably with a resistance value of about 100 Ohms, to the conducting layer 25 of the second electrode assembly 23 shown in FIG. 1. The high voltage terminal of the power supply 33 is connected directly to the conducting layer 15 of the first electrode assembly 13 to complete the circuit. If the resistance between gate and source of the JFET 53 is increased or decreased by a variable resistor 51, the charge flowing from source to drain will decrease or increase, respectively, in a predictable manner. Thus, a means is provided to increase or decrease the current, and thus to control the rate at which the medicament enters the body through iontophoretic action.

Figure 4:
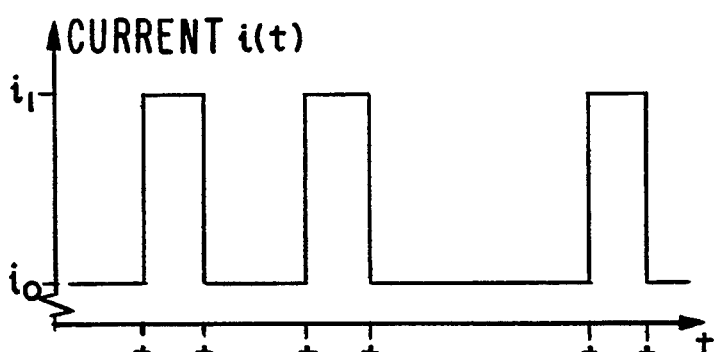
FIG. 4 is a graphical view of medicament that might be delivered, as a function of time, in a patient-controlled indicator system according to the invention.

In some instances it may be desirable to allow a patient to self-administer a bolus dose of medication, such as an analgesic, during periods of severe pain. Such a device would have control features that allow the patient to deliver such medicament at a rate greater than the long term rate for short periods of time. This increased delivery rate may be implemented, upon demand by the patient at a time $t = t_1$, by increase of the current i(t) delivered to the iontophoretic cell from the long term current value $i_0$ to a larger current value $i_1$, corresponding to delivery of a "bolus" dose to the patient, for a time interval $t_1 \leq t \leq t_2$ of fixed length $\Delta t = t_2 - t_1$, as illustrated in FIG. 4. Subsequent demands for increased delivery rate at later times $t = t_3$ and $t = t_5$ will result in new increases of the current value from $i_0$ to $i_1$ over the time intervals $t_3 \leq t \leq t_4$ and $t_5 \leq t \leq t_6$, where the time interval lengths $t_4 - t_3 = t_6 - t_5 = \Delta t$ = constant. In practice, the time interval length $\Delta t$ can cover a broad range. In a more sophisticated version, if the patient has demanded and received medicament at an increased rate corresponding to the current $i_1$ for a time interval $t_1 \leq t \leq t_2$, the patient might be "locked out" so that the system would not respond to another such demand for a time interval $t_2 \leq t \leq t_3$, where $t_3 - t_2$ is predetermined.

Figure 5:
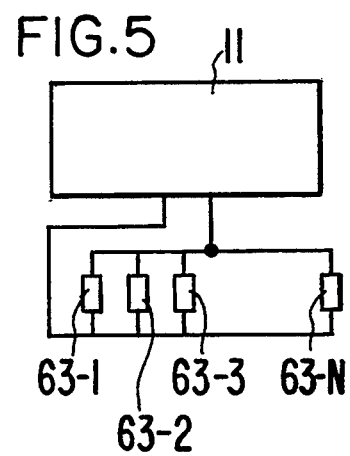
FIG. 5 illustrates one implementation of quantitative encoding and display according to the invention.

FIG. 5 illustrates an embodiment 61 of a visual indicator for iontophoretic delivery of medicaments or drugs to a patient, in which precisely one of a plurality of N light emitting diodes, liquid crystals or other suitable visual indicators (collectively referred to as "visible light devices" or "VLDs" herein for convenient reference) 63-1, 63-2, 63-3, . . . 63-N is lit (or otherwise activated), corresponding to the cumulative amount of medicament delivered to the patient in a predetermined time interval, such as 24 hours. A VLD, when lit, would indicate that an amount (mass) of medicament $\Delta\mu$ lying in a range $\Delta\mu_n < \Delta\mu \leq \Delta\mu_{n+1}$ (n=1, 2, ..., N) has been delivered, where $\Delta\mu_1 < \Delta\mu_2 < ... \Delta\mu_N$. In one mode of operation of this embodiment, each of the plurality of VLDs would, when lit, display a color that is visually distinguishable from the color of each of the other VLDs. For example, the colors of the VLDs 63-1, 63-2, 63-3, ..., 63-N might be blue, blue green, green, ..., and red, respectively, so that a person monitoring the VLD display could immediately visually determine the range of the cumulative medicament delivered. The order of arrangement of colored, visually distinguishable VLDs is not importance in this mode.

In a second mode of this embodiment, the N VLDs may be ordered or numbered 1, 2, ..., N and encoded binarily to provide a more precise measure of the cumulative amount of medicament delivered. For example, if the cumulative amount of medicament delivered $\Delta\mu$ satisfies the inequalities $$\Delta\mu_0 \sum_{k=1}^{N} [n_k/2^k] < \Delta\mu \leq \Delta\mu_0 \left( \sum_{k=1}^{N} [n_k/2^k] + 1/2^N \right), \quad (5)$$

where $\Delta\mu_0$ is the maximum value of the quantity $\Delta\mu$ deliverable and each of the quantities $n_k$ is either 0 or 1, VLD 63-k could be illuminated if $n_k=1$ and could be non-illuminated if $n_k=0$. For example, if N=4 and VLDs 63-1 and 63-3 are the only VLDs illuminated, this would indicate that the quantity $\Delta\mu$ lies in the range $0.625 \mu_0 < \Delta\mu < 0.75 \mu_0$, corresponding to the binary 1 0 1 0.

One advantage of this mode is that the cumulative amount of medicament delivered is displayed with improved accuracy, with an error of no more than $\Delta\mu_0/2^N$. The VLD pattern is encoded digitally here, using a base of two ($n_k=0$ or 1). Any other suitable integer base P (P$\geq$2) could also be used. Here, more than one VLD could be simultaneously illuminated and the VLDs would not be color coded so that it might not be possible to visually determine or estimate the cumulative amount of medicament delivered at a glance. This could be advantageous, if information on the cumulative amount of medicament delivered is not to be shared with the patient.

A third mode of the embodiment 61 shown in FIG. 5 would merely illuminate a single one of the VLDs, as in the first mode, but the VLDs would not be color coded. The VLDs in this mode would be ordered 1, 2, ..., N, and the position of the particular VLD that is lit would determine the range of the cumulative amount of medicament delivered.

In a fourth mode of the embodiment 61, using N=4 VLDs of no particular color or colors, the four VLDs would be ordered and digitally encoded as in the second mode, but the four-place binary code ($n_1$, $n_2$, $n_3$, $n_4$) would be interpreted as follows.

| Group | | Status | | Interpretation |
|---|---|---|---|---|
| $n_1$ | $n_2$ | $n_3$ | $n_4$ | |
| 0 | 0 | 0 | 0 | System not functioning |
| 0 | 0 | 0 | 1 | Resistance too high; current not at desired level |
| 0 | 0 | 1 | 0 | Resistance too low; current terminated |
| 0 | 0 | 1 | 1 | System operating satisfactorily |
| 0 | 1 | 0 | 0 | Cumulative delivery is 0–25% |
| 0 | 1 | 0 | 1 | Cumulative delivery is 25–50% |
| 0 | 1 | 1 | 0 | Cumulative delivery is 50–75% |

-continued

| Group | | Status | | Interpretation |
|---|---|---|---|---|
| $n_1$ | $n_2$ | $n_3$ | $n_4$ | |
| 0 | 1 | 1 | 1 | Cumulative delivery is 75–100% |
| 1 | 0 | 0 | 0 | 0–25% of bolus dose utilized |
| 1 | 0 | 0 | 1 | 25–50% of bolus dose utilized |
| 1 | 0 | 1 | 0 | 50–75% of bolus dose utilized |
| 1 | 0 | 1 | 1 | 75–100% of bolus dose utilized |
| 1 | 1 | 0 | 0 | 75–100% of battery remains |
| 1 | 1 | 0 | 1 | 50–75% of battery remains |
| 1 | 1 | 1 | 0 | 25–50% of battery remains |
| 1 | 1 | 1 | 1 | Under 25% of battery remains |

This mode requires provision of a means to query the system and to provide signals to illuminate the appropriate VLDs. This indicator system divides naturally into four mutually exclusive groups of four indicia or binary signals each: (1) group 1 (binary values 0,1,2,3; $n_1=0$, $n_2=0$) displays the resistance values and functioning or malfunctioning of the system as a whole; (2) group 2 (binary values 4,5,6,7; $n_1=0$, $n_2=1$) displays the cumulative current delivered thus far; group 3 (binary values 8,9,10,11; $n_1=1$; $n_2=0$) displays the mount of bolus dose utilized thus far; and group 4 (binary values 12,13,14,15; $n_1=1$, $n_2=1$) displays the battery capacity remaining for the system. One button, corresponding to four different binary values, would be used to choose or to cycle through the four groups; and as each of the four groups is chosen, two VLDs would display one of the four ($=2^2$) status or condition indicia present within that group, using the indices $n_3$ and $n_4$.

The terms "drugs", "medicaments" and "therapeutic agents" are used interchangeably and are intended to have their broadest interpretation, namely any therapeutically active substance that is delivered to a living organism to produce a desire, usually beneficial, effect. This includes therapeutic agents in all the major therapeutic areas including, but not limited to: anti-infectives, such as antibiotics and antiviral agents; analgesics, including fentanyl, sufentanil, buprenorphine and analgesic combinations; anesthetics; anorexics; antiarthritics; antiasthmatic agents, such as terbutaline; anticonvulsants; antidepressants; antidiabetic agents; antidiarrheals; antihistamines; antiinflammatory agents; antimigraine preparations; antimotion sickness preparations, such as scopolamine and ondansetron; antinauseants; antineoplastics; antiparkinsonism drugs; antipruritics; antipsychotics; antipyretics; antispasmodics, including gastrointestinal and urinary; antocholinergics; sympathomimetrics; xanthine derivatives; cardiovascular preparations, including calcium channel blockers such as nifedipine; beta blockers; beta-agonists, such as dobutamine and ritodrine; antiarrythmics; antihypertensives, such as atenolol; ACE inhibitors, such as rinitidine; diuretics; vasodilators, including general, coronary, peripheral and cerebral; central nervous system stimulants; cough and cold preparations; decongestants; diagnostics; hormones, such as parathyroid hormone; hypnotics; immunosuppressives; muscle relaxants; parasympatholytics; parasympathomimetrics; prostaglandins; proteins; peptides; psychostimulants; sedatives; and tranquilizers.

The invention is also useful in the controlled delivery of peptides, polypeptides, proteins and other macromolecules. These macromolecular substances typically have a molecular weight of at least 300 Daltons, and more typically have a molecular weight of 300–40,000 Daltons. Specific examples of peptides and proteins in this size range include, without limitation, the following: LHRH; LHRH analogs, such as buserelin, gonadorelin; napharelin and leuprolide; GHRH; GHRF; insulin; insulotropin; heparin; calcitonin; octreotide; endorphin; TRH; NT-36 (chemical name is N=[[(s)-4-oxo-2-azetidinyl]carbonyl]-L-histidyl-L-prolinamide); liprecin; pituitary hormones, such as HGH, HMG, HCG and desmopressin acetate; follicle luteoids; aANF; growth factors, such as growth factor releasing factor (GFRF); bMSH: somatostatin; bradykinin; somatotropin; platelet-derived growth factor; asparaginase; bleomycin sulfate; chymopapain; cholecystokinin; chorionic gonadotropin; corticotropin (ACTH); erythropoietin; epoprostenol (platelet aggregation inhibitor); glucagon; hirulog; hyaluronidase; interferon; interleukin-1; interleukin-2; menotropins (urofollitropin (FSH) and LH); oxytocin; streptokinase; tissue plasminogen activator; vasopressin; desmopressin; ACTH analogs; ANP; ANP clearance inhibitors; angiotensin II antagonist; antidiuretic hormone agonists; antidiuretic hormone antagonists; bradykinin antagonists; CD4; ceredase; CSFs; enkephalins; FAB fragments; IgE peptide suppressors; IGF-1; neurotrophic factors; colony stimulating factors; parathyroid hormone and agonists; parathyroid hormone antagonists; prostaglandin antagonists; pentigetide; protein C; protein S; renin inhibitors; thymosin alpha-1; thrombolytics; TNF; vaccines; vasopressin antagonist analogs; alpha-1 anti-trypsin (recombinant); and TGF-beta.

Figure 6:
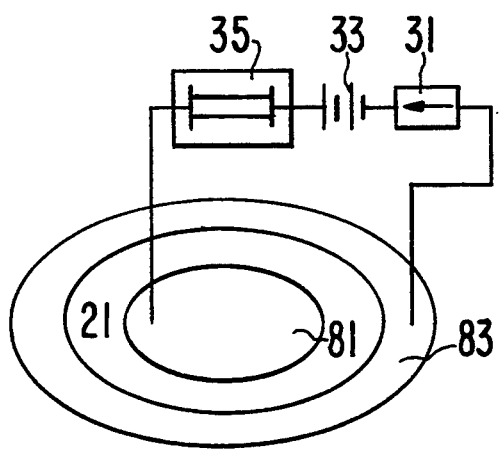

As an alternative to side-by-side alignment of the donor electrode assembly 13 and the counter electrode assembly 23, shown in FIG. 1, these electrode assemblies can be concentrically aligned, with the counter electrode assembly 81 being centrally positioned and being surrounded by an annular shaped donor electrode assembly 83, as shown in FIG. 6. The electrode assembly positions in FIG. 6 can be interchanged, with an annular shaped counter electrode assembly surrounding a centrally positioned donor electrode assembly. Alignment of the two electrode assemblies shown in FIG. 6 may be circular, elliptical, rectangular, or any other consistent geometric configuration.

The combined skin-contacting areas of the donor and counter electrode assemblies 13 and 15 in FIG. 1 can vary from 1 cm$^2$ to greater than 200 cm$^2$. A typical device will have donor and counter electrode assemblies with a combined skin-contacting area in the range of 5–50 cm$^2$.

Having thus generally described in detail our invention and certain embodiments thereof, it will be readily apparent that various modifications to the invention may be made by others skilled in the art without departing from the scope of this invention and which is limited only by the following claims.

We claim:

1. Iontophoresis apparatus that provides an indication of the cumulative amount of a therapeutic agent delivered through a body surface of a patient, the apparatus comprising:
   a first electrode assembly containing a therapeutic agent to be delivered and adapted to be placed in agent transmitting relation with a body surface of a patient;
   a second electrode assembly, adapted to be placed in ion transmitting relation with the body surface at a location spaced apart from the first electrode assembly;
   an electrical current source, electrically connected to the first and second electrode assemblies;
   a means for measuring the cumulative amount of electrical charge transferred during operation of the apparatus over a given time period which cumulative charge transferred is a measurement of cumulative amount of agent delivered; and
   means for displaying a visually perceptible output of the cumulative amount of agent delivered, said display means being electrically connected in parallel with the current source.

2. The apparatus of claim 1, wherein said display means has a first terminal and a second terminal and displays the cumulative amount of electrical charge transferred between the first and second terminals.

3. The apparatus of claim 2, wherein said measuring means and display means comprise an anode having a selected metal coating on its surface and electrically connected to one of said first terminal and said second terminal, a cathode electrically connected to the other of said first terminal and said second terminal, and an electrolyte solution that surrounds at least a portion of the anode and the cathode and provides an electrically conducting path between the anode and the cathode and provides a path for transport to the cathode of ions of the selected metal of the anode coating, wherein visually perceptible amounts of metal are deposited at the cathode, which deposition occurs upon reduction of metal cations at the cathode during agent delivery.

4. The apparatus of claim 3, wherein said selected metal for said anode coating is selected from the group consisting of copper, silver, nickel, mercury, chromium, iron, lead and tin.

5. The apparatus of claim 3, wherein said electrolyte solution comprises an aqueous solution of a water-soluble salt.

6. The apparatus of claim 3, wherein said electrolyte solution is selected from the group consisting of sulfuric acid, citric acid, phosphoric acid, pyrophosphoric acid, fluoboric acid, oxalic acid cyanide and ammonium hydride.

7. The apparatus of claim 3, wherein said electrolyte solution includes dissolved metal ions of a predetermined concentration, the metal ions being selected from the group consisting of copper, silver, nickel, mercury, iron, lead and tin.

8. The apparatus of claim 1, wherein said current source comprises a battery.

9. The apparatus of claim 8, wherein said current source further comprises current control means for limiting said current so that said current lies between predetermined lower and upper limits.

10. The apparatus of claim 8, wherein said current source includes current control means for controlling said current in a determinable, time-varying manner.

11. The apparatus of claim 10, wherein said current control means comprises:
    a resistor, having a first terminal and a second terminal, with its first terminal connected to said current source;
    a junction field effect transistor, having a source, a gate and a drain, having its source electrically connected to the second terminal of the resistor, having its gate electrically connected to the first terminal of the resistor, and having its drain electrically connected to said first electrode assembly.

12. The apparatus of claim 11, wherein said resistor is a variable resistor having a predetermined range of resistance values.

13. The apparatus of claim 11, wherein said current control means further comprises a second resistor of predetermined resistance value that is connected between said drain of said field effect transistor and one of said fast and second electrode assemblies.

14. The apparatus of claim 10, wherein said current control means comprises:
   a resistor, having a fast terminal and a second terminal, with its first terminal connected to said current source;
   a junction field effect transistor, having a source, a gate and a drain, having its source electrically connected to the second terminal of the resistor, having its gate electrically connected to the first terminal of the resistor, and having its drain electrically connected to one of said first and second electrode assemblies.

15. The apparatus of claim 14, wherein said resistor is a variable resistor having a predetermined range of resistance values.

16. The apparatus of claim 14, wherein said current control means further comprises a second resistor of predetermined resistance value that is connected between said drain of said field effect transistor and one of said fast and second electrode assemblies.

17. The apparatus of claim 10, wherein said current control means includes patient-activated signal means, connected to said current source, for delivering increased current of a predetermined magnitude for a time interval of predetermined delivery length when the patient-activated signal means is activated by the patient.

18. The apparatus of claim 17, wherein said current control means delivers increased current of approximately constant magnitude during at least a portion of said time interval.

19. The apparatus of claim 17, wherein said patient-activated signal means includes lock-out means for precluding delivery of said current of increased magnitude for a time interval of a predetermined lock-out length after said patient-activated signal means has been activated and has delivered said current of increased magnitude.

20. The apparatus of claim 1, wherein said cumulative amount of electrical charge delivered by the apparatus is divided into a plurality of non-overlapping ranges, the apparatus further comprising a plurality of activatable visible light devices, each such visible light device corresponding to a different one of the non-overlapping ranges of said cumulative amount of electrical charge delivered.

21. The apparatus of claim 20, wherein said plurality of activatable light devices displays light having a visually distinguishable color and is controlled by said display means, whereby if said cumulative amount of electrical charge delivered lies in one of said non-overlapping ranges, one of said visible light devices displays light of a visually distinguishable color.

22. The apparatus of claim 20, wherein said cumulative amount of electrical charge delivered by the apparatus is divided into a plurality of N non-overlapping ranges, the apparatus further comprising a plurality of N activatable visible light devices, numbered 1, 2, ... N, with each of said visible light devices corresponding to a different one of the non-overlapping ranges of said cumulative amount of electrical charge delivered and being controlled and activated by said display means, whereby if said cumulative amount of electrical charge delivered lies in one of the non-overlapping ranges, one visible light device is activated and displays light.

23. The apparatus of claim 1, wherein said cumulative amount of electrical charge, denoted $\Delta\mu$, delivered by the apparatus is divided into a plurality of approximately $2^N$ non-overlapping ranges with a maximum value of $\mu_0$, where N is a predetermined positive integer, the apparatus further comprising a plurality of at least N activatable visible light devices, numbered k=1, 2, ... N, that are controlled by said display means so that if $\Delta\mu$ satisfies the inequalities $$\Delta\mu_0 \sum_{k=1}^{N} [n_k/2^k] < \Delta\mu \leq \Delta\mu_0 \left( \sum_{k=1}^{N} [n_k/2^k] + 1/2^k \right),$$

with each coefficient $n_k=0$ or 1, visible light device number k is activated if $n_k=1$ and is inactivated if $n_k=0$.

24. The apparatus of claim 1, wherein said cumulative amount of electrical charge, denoted $\Delta\mu$, delivered by the apparatus is divided into a plurality of approximately $2^N$ non-overlapping ranges with a maximum value of $\mu_0$, where N is a predetermined positive integer, the apparatus further comprising a plurality of at least N activatable visible light devices, numbered k=1, 2, ..., N, that are controlled by said display means so that if $\Delta\mu$ satisfies the inequalities $$\Delta\mu_0 \sum_{k=1}^{N} [n_k/2^k] < \Delta\mu \leq \Delta\mu_0 \left( \sum_{k=1}^{N} [n_k/2^k] + 1/2^k \right),$$

with each coefficient $n_k=0$ or 1, visible light device number k is activated if $n_k=0$ and is inactivated if $n_k=1$.

25. The apparatus of claim 1, wherein the apparatus has a plurality of L operating conditions associated therewith and numbered j=1, 2, ..., L, where L is a positive integer satisfying the inequalities $2^{M-1} < L \leq 2^M$ for a predetermined positive integer M, the apparatus further comprising a plurality of M activatable visible light devices, numbered m=1, 2, ..., M and controlled by said display means, so that, if operating condition number j is present and the number j is expressible as $$j = \sum_{m=1}^{M} (2)^{n_m},$$

where $n_m=0$ or $n_m=1$, visible light device number m is activated if $n_m=1$ and is not activated if $n_m=0$.

26. The apparatus of claim 1, wherein the apparatus has a plurality of L operating conditions associated therewith and numbered j=1, 2, ..., L, where L is a positive integer satisfying the inequalities $2^{M-1} < L \leq 2^M$ for a predetermined positive integer M, the apparatus further comprising a plurality of M activatable visible light devices, numbered m=1, 2, ..., M and controlled by said display means, so that, if operating condition number j is present and the number j is expressible as $$j = \sum_{m=1}^{M} (2)^{n_m},$$

where $n_m=0$ or $n_m=1$, visible light device number m is activated if $n_m=0$ and is not activated if $n_m=1$.

27. The apparatus of claim 1, wherein said first electrode assembly comprises an electrically conducting layer and an ionically conducting layer that contains said therapeutic agent in an ionized or ionizable form.

28. The apparatus of claim 1, wherein said first electrode assembly further comprises an ionically conducting adhesive layer, positioned between and electrically connected to said first electrode assembly and said body surface of said patient 29. The apparatus of claim 1, wherein said second electrode assembly comprises an electrically conducting layer and an ionically conducting layer that contains an electrolyte in ionized or ionizable form.

30. The apparatus of claim 1, wherein said first electrode assembly further comprises an ionically conducting adhesive layer, positioned between and electrically connected to said second electrode assembly and said body surface of said patient.

31. The apparatus of claim 1, wherein the cumulative amount of therapeutic agent delivered through the body surface is substantially directly proportional to the cumulative amount of charge transferred through the apparatus.

32. The apparatus of claim 1, wherein said display means comprises a plurality of visible light emitting devices and means for activating each of the devices at different non-overlapping ranges of cumulative electrical charge passed through the apparatus.

33. The apparatus of claim 32, wherein each of said plurality of visible light emitting devices displays a light having a color visually distinguishable from the other visible light emitting device.

* * * * *

UNITED STATES PATENT AND TRADEMARK OFFICE
CERTIFICATE OF CORRECTION

PATENT NO. : 5,445,606
DATED      : August 29, 1995
INVENTOR(S): Haak et al.

It is certified that error appears in the above-indentified patent and that said Letters Patent is hereby corrected as shown below:

In column 15, lines 8, 11, and 28, "fast" should read --first--.

Signed and Sealed this

Twelfth Day of December, 1995

Attest:

BRUCE LEHMAN

*Attesting Officer*       *Commissioner of Patents and Trademarks*

Disclaimer

5,445,606 — Ronald P. Haak, San Jose; Felix Theeuwes, Los Altos, both of Calif.; David K. Roe, Portland, Oreg. INDICATOR FOR IONTOPHOREIS SYSTEM, Patent dated Aug. 29, 1995. Disclaimer filed Jan. 10, 2005, by the Assignee, ALZA Corporation.

The term of this patent, subsequent to the term number 5,246,417 has been disclaimed.

*(Official Gazette May 10, 2005)*

UNITED STATES PATENT AND TRADEMARK OFFICE
CERTIFICATE OF CORRECTION

PATENT NO. : 5,445,606 Page 1 of 1
APPLICATION NO. : 08/069061
DATED : August 29, 1995
INVENTOR(S) : Haak et al.

It is certified that error appears in the above-identified patent and that said Letters Patent is hereby corrected as shown below:

On the title page, the "[*] Notice" should read as the following:

-- [*] Notice: The term of this patent, subsequent to the term of patent number 5,246,417 has been disclaimed. --

Signed and Sealed this

Twenty-second Day of August, 2006

JON W. DUDAS
*Director of the United States Patent and Trademark Office*